United States Patent [19]

Hammen et al.

[11] Patent Number: 5,347,034

[45] Date of Patent: Sep. 13, 1994

[54] PROCESS FOR THE PRODUCTION OF POLY(O-ALKYLURETHANES) OF THE DIPHENYL METHANE SERIES

[75] Inventors: Günter Hammen, Rommerskirchen; Thomas Schieb, Roesrath; Stefan Wershofen, Moenchengladbach, all of Fed. Rep. of Germany

[73] Assignee: Bayer Aktiengesellschaft, Leverkusen, Fed. Rep. of Germany

[21] Appl. No.: 871,914

[22] Filed: Apr. 21, 1992

[30] Foreign Application Priority Data

Apr. 23, 1991 [DE] Fed. Rep. of Germany ....... 4113156

[51] Int. Cl.$^5$ ............................................. C07C 261/00
[52] U.S. Cl. ......................................... 560/25; 560/24
[58] Field of Search ...................... 560/24, 25, 27, 29

[56] References Cited

U.S. PATENT DOCUMENTS 3,763,217 10/1973 Brill .................................. 260/471 C
4,450,188 5/1984 Kawasumi ........................... 427/217

FOREIGN PATENT DOCUMENTS 1166649 5/1984 Canada .
065026 11/1982 European Pat. Off. ............. 560/24
8805430 7/1988 European Pat. Off. .
391473 10/1990 European Pat. Off. .

*Primary Examiner*—José G. Dees
*Assistant Examiner*—Keith MacMillan
*Attorney, Agent, or Firm*—Joseph C. Gil; N. Denise Brown

[57] ABSTRACT

The present invention relates to an improved process for the production of monomeric and polymeric poly-(O-alkylurethanes) of the diphenyl methane series. The process comprises the reaction of the corresponding amines with dialkyl carbonates in the presence of a catalyst, followed by the isolation of the products in a highly pure form. The invention also relates to the use of the produced monomeric and polymeric poly(O-alkylurethanes) for the production of the corresponding isocyanates.

6 Claims, No Drawings

PROCESS FOR THE PRODUCTION OF POLY(O-ALKYLURETHANES) OF THE DIPHENYL METHANE SERIES

BACKGROUND OF THE INVENTION

The present invention relates to an improved process for the production of monomeric and polymeric poly-(O-alkylurethanes) of the diphenyl methane series by the reaction of the corresponding amines with dialkyl carbonates in the presence of a catalyst and isolation of the products in a very pure form. The invention also relates to the use of the products for the production of the corresponding isocyanates.

The production of urethanes by reaction of amines with organic carbonates is known. Various methods are described in the literature for working up the reaction mixtures and isolating the products to obtain a certain degree of purity.

Monourethanes may be purified and isolated, for example, by distillation (DE 3,035,354, EP 0,323,514, EP 0,391,473). However, this method is not applicable to monomeric and polymeric poly(O-alkylurethanes) of the diphenyl methane series because these urethanes cannot be distilled without decomposition.

Recrystallization is another method of purifying the urethanes formed by the reaction of amines with carbonates. According to DE 2,160,111 (believed to correspond to U.S. Pat. No. 3,763,217), diphenyl urea formed as a secondary product is filtered off after the reaction of aniline with dimethyl carbonate, the filtrate is concentrated, and the residue is recrystallized from hexane to obtain N-phenyl-O-methylurethane. Even after recrystallization, however, the end product of this process still contains approximately 20% impurities in the form of N-alkylated anilines which are formed as secondary products during the reaction.

According to DE 3,035,354, 4,4'-bis'(butoxycarbonylamino)-diphenyl methane can be isolated after the reaction of 4,4'-diaminodiphenyl methane with excess dibutyl carbonate by taking up the reaction mixture in dichloromethane, filtering off the ureas, concentrating the filtrate, and recrystallizing the residue from a mixture of toluene and ligroin. The disadvantages of this process lie in the poor yield of diurethane (only 17% of the theoretical), and in the formation of large quantities of oligo- and polyureas which have to be converted into the diurethane in an additional process step. In addition, the mixture of dichloromethane and excess dibutyl carbonate which is formed while concentrating the filtrate has to be separated off by distillation.

U.S. Pat. No. 4,550,188 describes a similar process for isolating 4,4'-bis(ethoxycarbonylamino)diphenyl methane which is formed during the reaction of 4,4'-diaminodiphenyl methane with excess diethyl carbonate. The reaction solution is first mixed with water and the resulting mixture extracted with dichloromethane. The organic phase is dried over sodium sulfate and subsequently concentrated. The disadvantage of this process lies in the elaborate water-based working up phase using dichloromethane as the extractant. Before the excess diethyl carbonate is recycled, it has to be separated from the extractant by distillation. In addition, the end product of the process contains aminourethane and ureas (7.4%) and, also, small quantities of diamine (0.2%) as impurities in addition to 92.4% diurethane.

Accordingly, the problem addressed by the present invention was to provide a process for the production of monomeric and polymeric poly(O-alkylurethanes) of the diphenyl methane series which would make it possible to produce and isolate the products in a highly pure form by simple and efficient working up without any of the above described disadvantages of known processes. This problem has been solved by the process described below.

DESCRIPTION OF THE INVENTION

The present invention is directed to a process for the production of monomeric and polymeric poly(O-alkylurethanes) of the diphenyl methane series. More particularly, the process for the production of monomeric and polymeric poly(O-alkylurethanes) of the diphenyl methane series comprises reacting a) amines corresponding to the diphenyl methane series, including, for example, 4,4'-diaminodiphenyl methane, 2,4'-diaminodiphenyl methane, 2,2'-diaminodiphenyl methane, and higher homologs of these compounds as formed, for example, by the condensation of aniline with formaldehyde, and also mixtures thereof; with b) an excess of dialkyl carbonates containing from 1 to 2 carbon atoms per alkyl group, in the presence of c) a catalyst, such that the formed monomeric and/or polymeric poly(O-alkylurethanes) crystallize out in a highly pure form upon cooling. The produced poly(O-alkylurethanes) are cooled to temperatures of about 25 C. or lower, at pressures of 5-25 bar. Cooling is completed before the solution solidifies. Optionally, the monomeric and/or polymeric poly(O-alkylurethanes) may be separated off, for example, by filtration, after partial concentration of the reaction mixture. Depending on the solubility of the produced monomeric and/or polymeric poly(O-alkylurethanes), the solution may be partly concentrated to 10% by volume before cooling.

Suitable amines according to the process of the invention include, for example, 4,4'-diaminodiphenyl methane, 2,4'-diaminodiphenyl methane, 2,2'-diaminodiphenyl methane, and higher homologs of these compounds as formed, for example, by the condensation of aniline with formaldehyde (hereinafter referred to as polymer MDA), and mixtures thereof.

Suitable dialkyl carbonates include those corresponding to the following formula

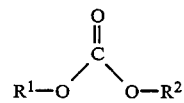

in which $R^1$ and $R^2$ may be the same or different, and each represents an alkyl radical containing from 1 to 2 carbon atoms.

Suitable catalysts include metal compounds. More particularly, suitable catalysts include metal compounds wherein said metal is selected from the group consisting of Groups 1 to 15 of the periodic table; preferably from the group consisting of Groups 12 and 14 of the periodic table; and most preferably from the group consisting of tin, zinc, and lead. The definition of Groups 1 to 15 of the periodic table above corresponds to the new IUPAC notation for the periodic table, which can be found in the Eleventh Edition of Hawley's Condensed Chemical Dictionary.

Examples of catalysts of the type in question include 1) Lewis acids such as, for example, salts or compounds of zinc, lead, titanium or zirconium; 2) organotin compounds such as, for example, dibutyl tin oxide or dibutyl tin dilaurate; and 3) basic compounds such as, for example, alkali metal or alkaline earth metal hydroxides or alkoxides.

Preferred catalysts include those catalysts which, if they remain in the product, do not adversely affect the subsequent decomposition of the urethanes formed during the reaction into the corresponding isocyanates and alcohols.

The catalysts are used in quantities of 0.01 to 20 mol-%, preferably in quantities of 0.05 to 15 mol-% and, more preferably, in quantities of 0.1 to 10 mol-%, based on the quantity of polyamine used.

The reaction temperatures are in the range of from about 70° to about 300° C., and preferably in the range of from about 100° to about 250° C. The process may be carried out at either normal or elevated pressures. Elevated pressure is necessary if low-boiling reactants are to be reacted at temperatures which exceed their boiling point(s).

In the reaction of a polyamine with a dialkyl carbonate, the reactants are generally used in quantities such that there is 1 mol of dialkyl carbonate to every gram equivalent of amino groups of the polyamine. In the practical application of the process according to the invention, the dialkyl carbonates are used in excess because excess dialkyl carbonate serves inter alia as a solvent. The alcohol formed during the reaction in accordance with the following equation (which is merely intended to illustrate the reaction principle)

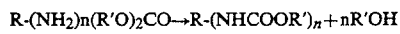

R-(NH$_2$)$_n$(R'O)$_2$CO→R-(NHCOOR')$_n$+nR'OH wherein
the substituents R and R' represent the inert residues of the reactants;
is removed by distillation, either continuously during the reaction, or at a suitable time after termination of the reaction. If the alcohol remains in the reaction mixture during the reaction, the intermediately formed ureas are converted by the alcohol into the urethane, so that there is generally no need for the ureas to be isolated and separately reacted.

It is surprisingly that, where a suitable excess of dialkyl carbonate is used (depending on the reactants), the monomeric and/or polymeric poly(O-alkylurethanes) formed in the process according to the invention crystallize out upon cooling. Optionally, after partial concentration of the reaction mixture, these poly(O-alkylurethanes) may be isolated in a highly pure form without the need for further purification. The isolated products of the process may contain part of the catalyst used, although this does not adversely affect the subsequent thermal decomposition of the urethanes into the corresponding isocyanates.

In addition to a small amount of monomeric and/or polymeric poly(O-alkylurethanes), the filtrate remaining after separation of the process products essentially contains aminourethanes and other secondary and intermediate products, which can be converted into monomeric and/or polymeric poly(O-alkylurethanes) by re-reaction with dialkyl carbonates, and, optionally, small quantities of the N-alkylated compounds. The filtrate may be reused in the process according to the invention, optionally, after the removal of alcohol formed during the reaction, and partial removal of the N-alkylated secondary products.

The process according to the invention may be carried out either continuously or discontinuously.

The urethanes produced by the process according to the invention may be used without further working up for the production of the corresponding isocyanates. The urethanes are converted by thermal decomposition into the corresponding isocyanates and alcohols, and the decomposition products formed are subsequently separated. Decomposition is carried out by heating to temperatures of from about 150° to about 450° C., pressures of from about 0.1 to 20 mbar, and either in the presence or absence of a solvent, depending on the urethane and its decomposition point.

The process according to the invention is illustrated by the following Examples.

EXAMPLES

Example 1

A mixture of 79.3 g (0.4 mol) 4,4'-diaminodiphenyl methane, 1,816 g (20.0 mol) dimethyl carbonate, and 1.73 g (2.0 mmol) Octa-Soligen Pb 24 is heated to 200° C. in a 3 liter autoclave. Octa-Soligen Pb 24 is a lead salt of 2-ethylhexanoic acid and isononanoic acid dissolved in gasoline. After 30 minutes, the reaction is terminated by cooling (yield: 94%, selectivity: 98%). The reaction mixture is then slowly cooled to 5° C. and the precipitate is filtered off. The precipitate is then washed with 100 ml dimethyl carbonate and dried, to yield 99.3 g of 4,4'-bis-(methoxycarbonyl-amino)-diphenyl methane (purity 99%, melting point 185° C.), corresponding to a yield of 79% of the theoretical yield. By recycling the filtrate, the yield of isolated 4,4'-bis-(methoxycarbonylamino)-diphenyl methane can be increased to more than 95% of the theoretical yield.

Example 2

A mixture of 79.3 g (0.4 mol) 4,4'-diaminodiphenyl methane, 1,890 g (16.0 mol) diethyl carbonate, and 3.46 g (4.0 mmol) Octa-Soligen Pb 24 is heated to 200° C. in a 3 liter autoclave. After 2 hours, the reaction is terminated by cooling (yield: 89%, selectivity: 98%). After filtration, the reaction mixture is concentrated in a water jet vacuum. The precipitate is filtered off, washed with 100 ml diethyl carbonate and dried, to yield 108.6 g of 4,4'bis(ethoxycarbonylamino)-diphenyl methane (purity 99%, melting point 131° C.), corresponding to a yield of 79% of the theoretical yield. By recycling the filtrates, the yield of isolated 4,4'-bis-(ethoxycarbonylamino)-diphenyl methane can be increased to more than 95% of the theoretical yield.

Although the present invention has been described in detail in the foregoing for the purpose of illustration, it is to be understood that such detail is solely for that purpose and that variations can be made therein by those skilled in the art without departing from the spirit and scope of the invention except as it may be limited by the claims.

We claim:
1. A process for the production of monomeric and/or polymeric poly(O-alkylurethanes) of the diphenyl methane series comprising reacting
    a) amines selected from the group consisting of 4,4'-diaminodiphenyl methane, 2,4'-diaminodiphenyl methane, 2,2'-diaminodiphenyl methane, higher homologs thereof formed in the condensation of aniline with formaldehyde, and mixtures thereof; with b) a dialkyl carbonate containing from 1 to 2 carbon atoms per alkyl group;

in the presence of c) a catalyst;

wherein said dialkyl carbonate is present in a quantity such that the molar ratio of dialkyl carbonate to amine is at least 40:1, and the formed monomeric and/or polymeric poly(O-alkylurethanes) crystallize out in a highly pure form upon cooling.

2. The process of claim 1, wherein said catalyst is a metal compound selected from the group consisting of Groups 1 to 15 of the periodic table.

3. The process of claim 1, wherein said catalyst is a metal compound selected from the group consisting of Group 12 of the periodic table, and Group 14 of the periodic table.

4. The process of claim 1, wherein said catalyst is a metal compound selected from the group consisting of tin, zinc, and lead.

5. The process of claim 1, wherein said formed monomeric and/or polymeric poly(O-alkylurethanes) are separated off after partial concentration of the reaction mixture.

6. In a process for the production of an isocyanate comprising heating a urethane, the improvement wherein said urethane is a monomeric and/or polymeric poly(O-alkylurethane) produced by the process of claim 1.

* * * * *